US008653293B2

(12) United States Patent
Wynne et al.

(10) Patent No.: US 8,653,293 B2
(45) Date of Patent: Feb. 18, 2014

(54) MOBILE SELF-SPREADING BIOCIDES

(71) Applicants: James H Wynne, Alexandria, VA (US); Ramesh R. Pant, Fairfax, VA (US)

(72) Inventors: James H Wynne, Alexandria, VA (US); Ramesh R. Pant, Fairfax, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/735,188

(22) Filed: Jan. 7, 2013

(65) Prior Publication Data

US 2013/0123531 A1 May 16, 2013

Related U.S. Application Data

(60) Division of application No. 12/748,752, filed on May 21, 2010, now Pat. No. 8,362,290, which is a continuation of application No. 11/749,252, filed on May 16, 2007, now Pat. No. 7,741,503.

(60) Provisional application No. 60/826,569, filed on Sep. 22, 2006.

(51) Int. Cl.

| | |
|---|---|
| ***C07F 7/10*** | (2006.01) |
| ***C07F 7/08*** | (2006.01) |
| ***C07F 7/18*** | (2006.01) |

(52) U.S. Cl.

USPC ............................ 556/424; 556/423; 556/425

(58) Field of Classification Search

None

See application file for complete search history.

(56) References Cited

PUBLICATIONS

Oosterhof et al. Applied and Environmental Microbiology, 2006, 72(5), 3673.*

* cited by examiner

*Primary Examiner* — Yevegeny Valenrod

(74) *Attorney, Agent, or Firm* — US Naval Research Laboratory; Joseph T. Grunkemeyer

(57) ABSTRACT

A compound having the formula:

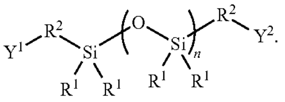

Each $R^1$ is $C_1$-$C_3$ alkyl group or fluoridated $C_1$-$C_3$ alkyl group. The value n is a positive integer. Each $R^2$ is alkylene group or polyethylene glycol group. $Y^1$ is hydrogen, quaternary ammonium containing group, or phenol-containing group. $Y^2$ is quaternary ammonium-containing group or phenol-containing group. The quaternary ammonium-containing group is non-aromatic and contains no more than one quaternary ammonium.

2 Claims, 3 Drawing Sheets

MOBILE SELF-SPREADING BIOCIDES

This application is a divisional application of U.S. patent application Ser. No. 12/748,752, allowed and filed on May 21, 2010, which is a continuation application of U.S. Pat. No. 7,741,503, issued on Jun. 22, 2010, which claims the benefit of U.S. Provisional Patent Application No. 60/826,569, filed on Sep. 22, 2006, incorporated herein by reference.

FIELD OF THE INVENTION

The invention is generally related to biocidal surface treatment.

DESCRIPTION OF RELATED ART

Decontamination is a complex process that frequently involves multiple technologies and approaches, depending on the nature and extent of the contamination. Currently, tons of decontaminating agents and the solvents used to disperse them must be transported to the contaminated area for use. Frequently the actual bacteria or other contamination is in inaccessible locations thus making complete decontamination very difficult. Furthermore, many decontaminating chemical agents rely upon generation of very reactive species and are, therefore, inherently unstable. Most commercial sterilants require activation just prior to use and lose effectiveness within hours. The efficacy of some agents such as hypochlorites is rapidly attenuated by the presence of organic matter and requirement of moisture for distribution. Use of moisture alone in confined spaces frequently results in mold and bacteria growth. Bactericidal efficacy also requires very careful attention to personnel safety. A variety of aldehydes have shown effectiveness at relatively high concentrations (2-10%) as liquids and requires a minimal amount of humidity for effectiveness as vapor. Air duct decontamination has utilized extremely toxic gases such as ethylene oxide, chlorine dioxide and methylene bromide. Spores and mold pose a particularly difficult and unexpected problem with respect to monitoring the success of the decontamination efforts. Thus, a more effective, simple system for decontaminating surfaces is needed.

The ability to disinfect surfaces and manufacture self-decontaminating surfaces is an area of research that has received much attention in recent years (Decraene et al., *Appl. Environ. Microbiol.,* 72, 4436 (2006); Punyani et al., *J. Appl. Polym. Sci.,* 102, 1038 (2006); Xu et al., *J. Macromolecules,* 34, 337 (2001). All publications and patent documents referenced throughout are incorporated herein by reference.). Applications for such products include hospital surfaces, medical implants, children's toys (Nzeako et al., *Br. J. Biomed. Sci.,* 63, 55 (2006); Lee, International Patent Application Publication No. WO00/02636 (2000)), public transportation surfaces, and food preparation areas (Tune et al., *J. Infect.,* 53, 140 (2006); Bower et al., *Int. J. Food Microbial.,* 50, 33 (1999)). Although many of these surfaces can be cleaned through the use of topical disinfectants, the ability to continuously self-disinfect is particularly desirable with respect to long term maintenance costs associated with repeated topical surface disinfection Furthermore, the ability to disinfect surfaces that cannot be easily accessed would be extremely advantageous from an economic standpoint.

Polydimethylsiloxanes (PDMS) have been used in many applications as a result of their commercial availability and physical properties such as low surface energy and versatility in wetting a variety of surfaces (Saritha et al., *Polymer,* 47, 6263 (2006)). Moreover, a significant amount of attention has recently been directed toward the development of a novel class of PDMS-based biocides due to increased potential for microbial contamination and infectious risks to military personnel and the general public (Kim et al., *J. Biotechnol.,* 9, 176(2006)). In a recent study, Baney and coworkers (Kim et al) demonstrated a unique class of biocides based on simple silicone chemistry derived from sitanol intermediates. The silanols exhibited activity against both Gram-negative and Gram-positive bacteria and are considered environmentally benign.

In another report, quaternary ammonium silane-based biocides were used to coat silicone rubber shunt prosthesis, yielding a positively charged, antimicrobial surface (Oosterhof et at., *Appl. Environ. Microbiol.,* 72, 3673 (2006)). The antimicrobial properties of positively-charged surface treatments are discussed in the context of multiorganism containing biofilms. Although the biocidal effect observed with this treatment could not be directly attributed to the positively charged surface, the study provides useful insights for applications where multiorganism biofilms present a risk for infection.

In U.S. Pat. No. 6,465,409, Carr et al. described a novel aqueous biocide system composed of a water-soluble biocide and a polyorganosilaxane. The two components are combined and sprayed onto hard surfaces for disinfecting. The biocide is slowly released upon contact with water after drying on the deposited surface. Although a unique approach, the method lacks utility with respect to the decontamination of inaccessible surfaces and surfaces with preexisting contamination.

Work to formulate reloadable antimicrobial coatings based on amphiphilic silicone networks has been reported (Tiller et al, *J. Surf. Coat. Int. Part B: Coat. Trans.,* 88, 49 (2005)), in which a thin, covalently, surface-attached coating was applied. Both hydrophobic and hydrophilic surfaces are present and demonstrate nanophase morphology. These coatings have shown antimicrobial activity against the bacterium *Staphylococcus aureus*, even after washing. This work appears promising; however, a major drawback of the method is that the coatings are difficult to apply to surfaces.

Hathorne et al., "Investigation of the impact of aging on the efficacy of several commercial biocides (abstracts of papers). In the 231st ACS National Meeting, Atlanta, Ga., Mar. 26-30, 2006, likewise, reported a study of latex degradation by microbial action. The focus was to determine how the structure and morphology of surfactants with ionic and nonionic end groups impact the efficacy of several biocides. The surfaces were successfully evaluated against *Pseudomonas aeruginosa* and *Escherichia coli*. Autoclaving and heating the material had a great impact on the efficacy of the performance. This approach demonstrates that the degradation of latex by bacteria is frequently avoided; however, it does not demonstrate self-disinfection of the surface and ultimately requires heat activation.

Polyquaternary ammonium compounds have been prepared and evaluated as microbiocides, corrosion inhibitors, debonding agents, flocculants, softeners, antistatic agents, and demulsifiers (Fenyes et al., U.S. Pat. No. 4,506,081). Although successful in the described applications, these molecules are not mobile or self-spreading. Polysiloxanes bearing both primary alcohols and quaternary ammonium salts were incorporated in polyurethane films. Because the polyquats were covalently bound to the resin system, they were effective in place, yet lacked mobility (Hazziza-Laskar et al., *J. Appl. Polym. Sci.,* 58, 77 (1985)). Similarly, the preparation of biocide-incorporated silicone coatings for antifouling/foul release applications also has been investigated by numerous groups (Clarkson, *Biofilms Bioadhesion Corrosion and Biofouling* 1999, 87). One group in particular has been successful in the synthesis of commercial biocides as alkyl moieties onto silicone backbones through covalent bonding and combinatorial schemes (Thomas et al. *Biofouling,* 20, 227 (2004); Stafslien et al., *J. Comb. Chem.,* 8, 156

(2006)). Synthetic control over the incorporation of crosslink functionalities within the polymer resin allowed tuning of the surface, the coating, and mechanical properties. Resistance to macrofouling was tested by static immersion tests, and preliminary results showed that the coatings prepared from biocide-incorporated silicones with the appropriate bulk modulus significantly reduced macrofouling. Silicone elastomers have also been used in many antifouling applications (Clarkson et al.). Their low surface energy and smooth surface is thought to weaken or eliminate the adhesive bond between fouling organisms and the coating, thereby allowing ships to be cleaned as they move.

SUMMARY OF THE INVENTION

The invention comprises a compound comprising the formula:

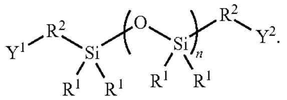

Each $R^1$ is an independently selected $C_1$-$C_3$ alkyl group or fluoridated $C_1$-$C_3$ alkyl group. The value n is a positive integer. Each $R^2$ is independently selected from alkylene group and polyethylene glycol group. $Y^1$ is hydrogen, quaternary ammonium-containing group, or phenol-containing group. $Y^2$ is quaternary ammonium-containing group or phenol-containing group. The quaternary ammonium-containing group is non-aromatic and contains no more than one quaternary ammonium.

The invention further comprises a polymer comprising the formula:

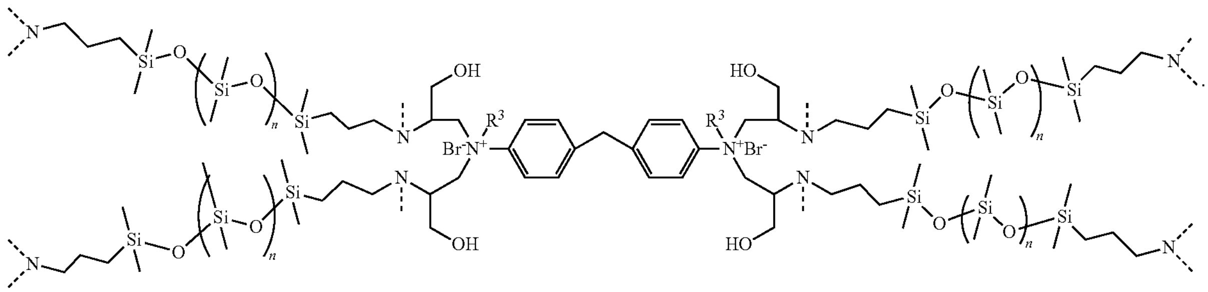

$R^3$ is an independently selected alkyl group. The value n is a positive integer. Each dashed bond indicates binding to a dipropyl polydimethylsiloxane group.

The invention further comprises a polymer comprising the formula:

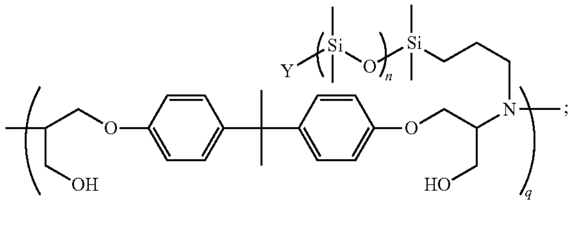

The values n and q are independently selected positive integers. Y is methyl or

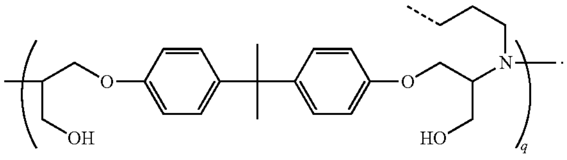

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

Figure 1:
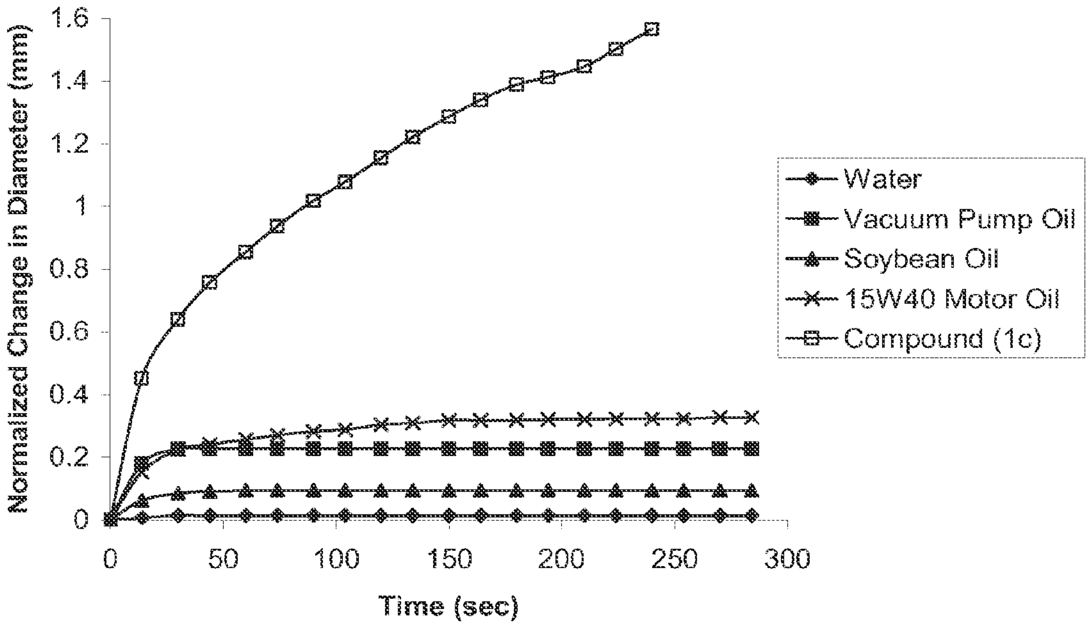
FIG. 1 shows a representation of the movement of a variety of commercial oils and water.

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

The disclosed potentially highly-mobile, self-spreading biocides combine the wetting and spreading properties of silicone fluids with biocidal functionalities of ammonium salts. The biocidal fluid may consist of three distinctive components: a polydimethylsiloxane (PDMS) block, an optional extender block, and a biocidal moiety. Each substructure may contribute a property and may balance this property against those of other substructures. The PDMS block of various chain lengths may provide the desired molecular mobility for the self-spreading coating characteristic. The extender block is a connecting structure between the silicone block and the biocide moiety and it also may have a chemical characteristic that promotes a chemical interaction between the biocide moiety and bacterial membranes. The type of the organic extension (i.e. $(CH_2)_n$, $(OCH_2CH_2)_n$) and length may be tailored to achieve optimum biological results while minimizing surface energy of the biocidal liquid. Lastly, the biocidal block comprises either a quaternary ammonium salt or a phenol. Both the quaternary ammonium salts and the phenols are classes of biocides that are well known for their antimicrobial properties against both Gram-positive and Gram-negative bacteria.

The compound may have the biocidal block on one or both sides of the PDMS moiety. Suitable $R^1$ include, but are not limited to, methyl and 3,3,3-trifluoropropyl. Suitable $R^2$ groups include, but are not limited to, methylene, 2-methyltrimethylene ($—CH_2—CH(CH_3)—CH_2—$), and polyethylene glycol (including oligomers and the single-mer). When $R^2$ is polyethylene glycol, the group ma be terminated on each end by any polyethylene glycol atom. The value n may be, but is not limited to, 1 to about 700.

Suitable quaternary ammonium groups include, but are not limited to, $—N^+R^3{}_3X^-$ and $—N^+(CH_3)_2R^3X^-$. Suitable phenol groups include, but are not limited to,

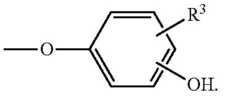

$R^3$ is an alkyl group and $X^-$ is a halide.

The quaternary ammonium compounds can generally be made by reacting the appropriate amino-PDMS with an alkyl bromide in methanol to convert the amino groups to quaternary ammonium groups as shown in Eq. (1). The amino-PDMS can also be reacted at the amine group with a quaternary ammonium-epoxy. The amino-PDMS compound may generally be made, for example, by reacting a lithiated PDMS with a chlorinated amine. The lithium and chlorine may also be reversed.

(1)

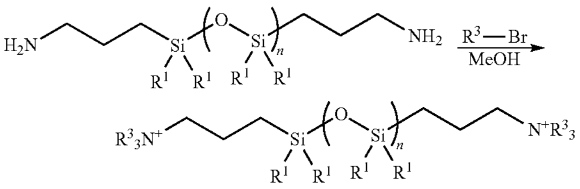

In a 25 mL round bottomed flask equipped with magnetic stir bar, Dean-Stark trap, and condenser were placed 4-hexylbenzene-1,3-diol (0.59 g, 6.25 mmol), an ethyleneoxide monomethylether (6.25 mmol), p-toluenesulfonic acid (0.01 g, 0.008 mmol), and 20 mL of toluene. An additional 7 mL of toluene was placed in the Dean-Stark trap to prevent taking the pot volume too low. The solution was allowed to reflux vigorously for 24 hours in an oil bath. The resulting solution was allowed to cool to room temperature and concentrated using the rotary evaporator. The resulting oil was eluted through a silica gel column employing a hexane/EtOAc (1:1) solvent system. The desired product eluted in the first fraction.

Example compounds are shown below. The values of m, n and p are positive integers.

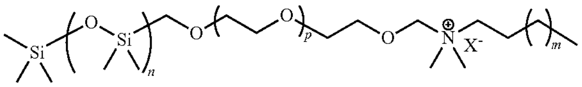

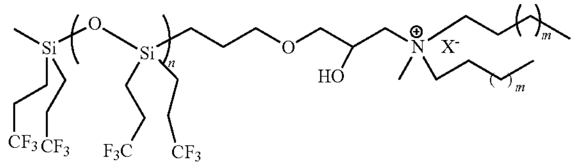

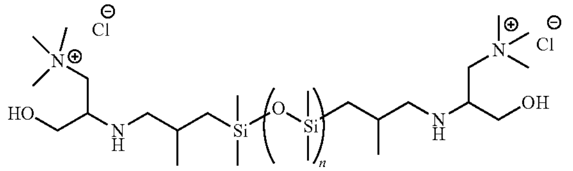

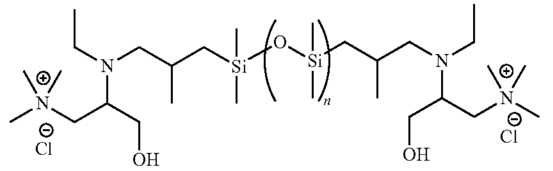

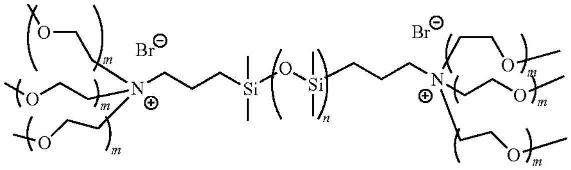

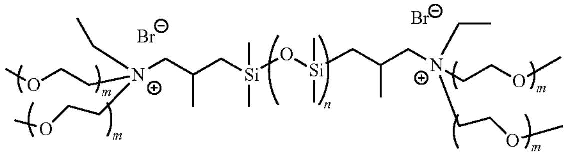

The use of the PDMS low energy backbone coupled with fewer quaternary ammoniums than in an ionic block copolymer PDMS may be advantageous. Functionalization at the termini of the PDMS backbone may deter coiling of the molecules, potentially resulting in an increase in the antimicrobial activity of the compounds.

The coating system may be of benefit on surfaces in which bacteria accumulate (i.e., air ducts, floors, clothing, etc.). The application of the liquid product may be facile, and the self-spreading capability may be an added benefit over current technologies. Potential features attractive for application include renewability, facile deposition, and minimal quantity required for surface coverage. The coating may be appropriate for a ceramic, metal, or polymer substrate and may be capable of neutralizing biological pathogens that come in contact with the coating surface, while being self-cleaned.

The compound may be used by applying to a surface upon which the biocidal effects are desired. The amount applied may be sufficient to produce at least a monolayer of the compound on a predetermined region upon self-spreading over a period of time of the compound over the region. Suitable surfaces include, but are not limited to, walls, floors, ceilings, and parts of an electronic apparatus. The compound may self spread to cover the walls, floors, and ceilings of an entire room or adjacent rooms or all the interior and exterior surfaces of the apparatus. For example, when applied to a computer, the compound may spread to cover the entire case and all the circuit boards and components inside the case An example of a potential use would be the cleaning of air ducts (commercial, residential, shipboard). Currently, a combination of methods including physically scraping the contamination from the surface, HEPA-filtration, heat-desiccation, and aerosolization of caustic chemical treatments are used. Some embodiments of the compound may be self-spreading fluid which contains a highly effective biocide that can be sprayed into an opening and quickly kills or neutralizes pathogens as they make contact with the mobile surface coating. The fluid is designed uniquely at the nanometer scale to position biocide compounds at the air interface in order to interact with pathogens and other contaminants present. The biocide is present in small quantities when compared to the bulk parent molecule; however, innovative surface-active features on the biocides enhance effectiveness.

As an alternative to the self-spreading compounds, the polymers described above may be used. A surface may be completely coated with the polymer at the outset, rather than relying on self-spreading effects. These polymers may be made as shown in Eqs (2)-(4).

(2)

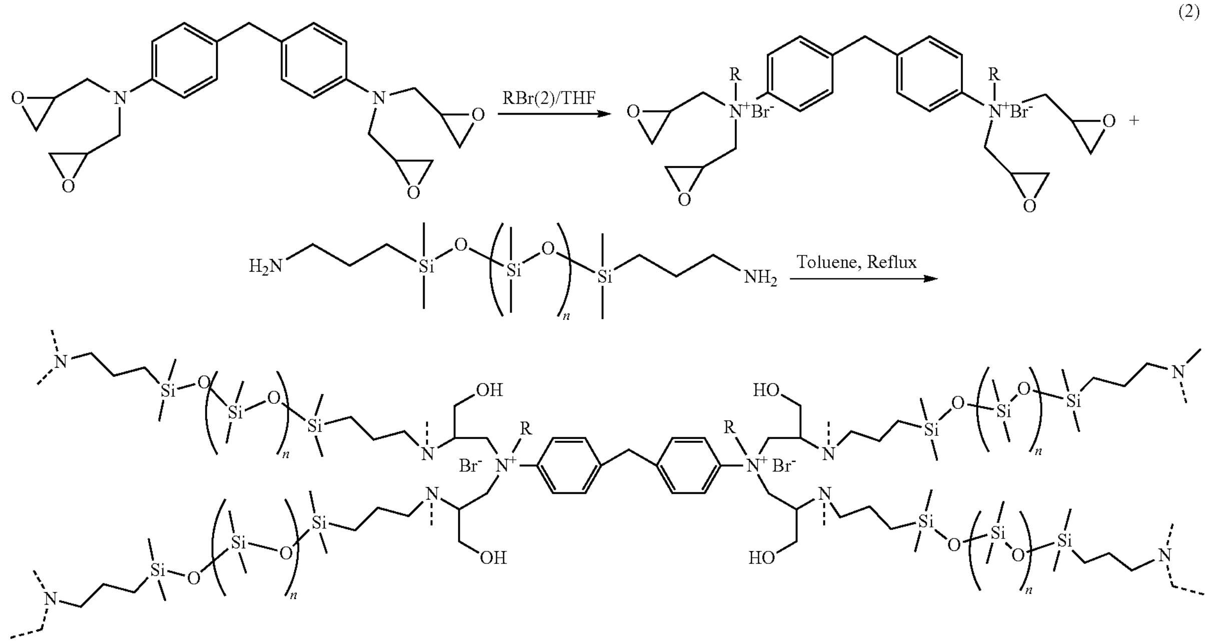

(3)

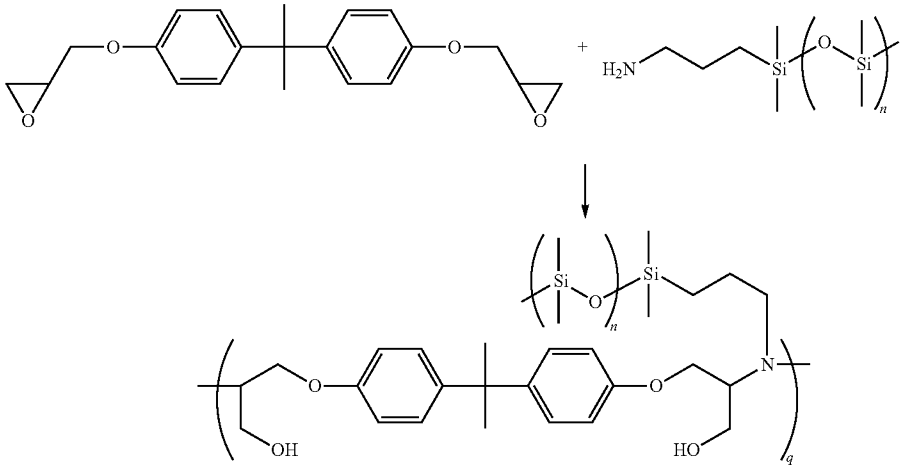

(4)

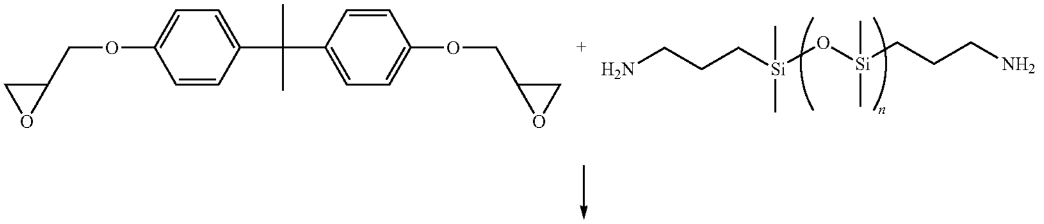

-continued

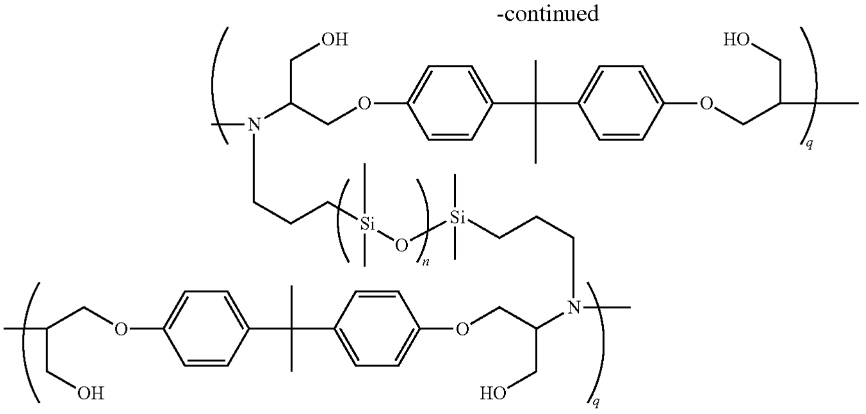

Having described the invention, the following examples are given to illustrate specific applications of the invention. These specific examples are not intended to limit the scope of the invention described in this application.

Materials—

All chemicals used were reagent grade and were purchased and used without further purification. Moisture sensitive reactions were conducted in oven-dried glassware under a nitrogen atmosphere. Unless otherwise noted, $^1H$ and $^{13}C$ NMR were taken in $CDCl_3$ at 300 MHz with a TMS internal standard. Chemical shifts are reported in units downfield from TMS. Coupling constants, J, are reported in units of Hertz (Hz). All $T_g$ data were recorded using standard DSC techniques and equipment. External elemental analyses were performed by Atlantic Microlab, Norcross, Ga. 30,091. Calculated percent elemental compositions were based on manufacturer's molecular weight range; albeit unknown as to the distribution. All new oligomers are reported within ±0.4%.

Example 1

General Procedure for the Preparation of Funetionalized PDMS Compounds from Primary Amines Into a 50-mL round bottom flask equipped with reflux condenser and magnetic stir bar were placed 2.0 mmol of primary diamino PDMS (Eq. (1)), 12.5 mmol of alkyl bromide, and 25 mL of methanol. The resulting solution was allowed to reflux for 18 h under nitrogen. An excess of alkyl halide was employed to facilitate the purification process. All solvent and unreacted alkyl halide (bp 37-215° C.) were evaporated under reduced pressure to afford the desired product in acceptable purity for this study. When desired, trituration of the reaction product with ethyl ether afforded a purer product.

Example 2

N,N,N-Triethyl-N-Propyl ammonium bromide terminated polydimethylsiloxanes (5a)

FTIR: 3414, 2960, 2898, 2794, 1593, 1408, 1266, 1104, 1015 $cm^{-1}$. $^1H$ NMR ($CDCl_3$): 3.24-2.93 (m, 16H), 1.92-1.85 (m, 4H), 1.57-1.40 (m, 18H), 0.67-0.55 (m, 4H), 0.14-0.05δ (m, 72H). A colorless viscous liquid was afforded in 70% yield. Anal. Calcd. range: C, 38.95-38.21; H, 8.77-8.70; N, 2.39-2.12. Found: C, 38.28; H, 8.32; N, 1.84.

Example 3

N,N,N,N-Tetrapropyl ammonium bromide terminated polydimethylsiloxanes (5b)

FTIR: 3420, 2960, 2898, 2802, 1943, 1604, 1447, 1404, 1262, 1108, 1004 $cm^{-1}$. $^1H$ NMR ($CDCl_3$): 3.02-2.91 (m, 16H), 2.04-4.83 (m, 16H), 1.06 (t, 18H), 0.66-0.58 (m, 4H), 0.18-0.04 δ (m, 72H). A pale yellow waxy solid was afforded in 65% yield. Anal. Calcd. range: C, 42.07-41.05; H, 9.15-9.04; N, 2.23-1.99. Found: C, 41.75; H, 8.83; N, 1.75.

Example 4

N,N,N-Tributyl-N-propyl ammonium bromide terminated polydimethylsiloxanes (5c)

FTIR: 3391, 2956, 2798, 1936, 1585, 1450, 1424, 1258, 1112, 1008 $cm^{-1}$. $^1H$ NMR (CDCl3): 3.12-2.95 (m, 16H), 1.94-1.83 (m, 16H), 1.52-1.42 (q, 12H), 1.07-0.94 (m, 18H), 0.65-0.60 (m, 4H), 0.20-0.14δ (m, 72H). A colorless solid was afforded in 62% yield. Anal. Calcd. range: C, 44.81-43.57; H, 9.48-9.34; N, 2.09-1.88. Found: C, 43.72; H, 9.42; N, 1.58.

Example 5

N,N,N-Tripentyl-N-propyl ammonium bromide terminated polydimethylsiloxanes (5d)

FTIR: 3422, 2968, 2798, 1939, 1593, 1454, 1412, 1258, 1119, 1004 $cm^{-1}$, $^1H$ NMR (CDCl3): 3.12-2.92 (m, 16H), 1.94-1.83 (m, 16H), 1.37 (m, 24H), 0.95-0.90 (m, 18H), 0.62-0.58 (m, 4H) 0.15-0.10δ (m, 72H). A colorless solid was afforded in 61%. Anal. Calcd. range: C, 47.22-45.82; H, 9.77-9.61; N, 1.97-1.78. Found: C, 45.48; H, 9.50; N, 1.60.

Example 6

N,N,N-Trihexyl-N-propyl ammonium bromide terminated polydimethylsiloxanes (5e)

FTIR: 3418, 2964, 2871, 2794, 1951, 1585, 1466, 1404, 1266, 1104, 1012 $cm^{-1}$. $^1H$ NMR (CDCl3): 3.03-2.98 (m, 16H), 1.91-1.83 (m, 16H), 1.34 (m, 36H), 0.90-0.89 (m, 18H), 0.66-0.58 (m, 4H), 0.14-0.01δ (m, 72H). A pale yellow waxy solid was afforded in 53% yield. Anal. Calcd. range: C, 49.36-47.84; H, 10.02-9.86; N, 1.86-1.69. Found: C, 47.67; H, 9.62; N, 1.92.

Example 7

N,N,N-Trioctadecyl-N-propyl ammonium bromide terminated polydimethyl siloxanes (5f)

FTIR: 3426, 2956, 2925, 2852, 1939, 1593, 1466, 1412, 1269, 1096, 1019 $cm^{-1}$. $^1H$ NMR (CDCl3): 2.99 (m, 16H), 2.15-1.94 (m, 16H), 1.33-1.23 (m, 180H), 0.88 (t, 18H), 0.21-0.01δ (m, 72H). A pale yellow solid was afforded in 35% yield. Anal. Calcd. range: C, 63.91-62.15; H, 11.77-11.57; N, 1.11-1.05. Found: C, 63.59; H, 11.61; N, 1.16.

Example 8

General Procedure for the Preparation of Funetionalized PDMS Compounds from Secondary Amines Into a 50-mL round bottom flask equipped with reflux condenser and magnetic stir bar were placed 2.0 mmol of secondary amino PDMS (Eq. (5)), 8.3 mmol of alkyl bromide, and 25 mL of methanol. The resulting solution was then allowed to reflux for 18 h under nitrogen. The solvent and excess unreacted alkyl bromide were evaporated under reduced pressure to afford the desired product that could be used without further purification. A purified product was obtained by trituration with ethyl ether.

(5)

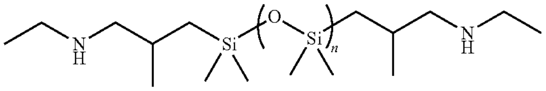

Example 9

N,N,N-Triethyl-N-isobutyl ammonium bromide terminated polydimethylsiloxanes (7a)

FTIR: 3414, 2960, 2898, 2794, 1593, 1408, 1266, 1104, 1015 $cm^{-1}$, $^1H$ NMR (CDCl3): 3.18-3.06 (m, 12H), 2.87-2.72 (m, 4H), 2.17 (m, 2H), 1.42 (t, 18H), 1.03 (d, 6H), 0.60-0.50 (m, 4H), 0.14-0.01δ (m, 66H). A colorless waxy solid was afforded in 86% yield, Anal. Calcd. range: C, 39.39-38.21; H, 8.81-8.70; N, 2.55-2.12. Found: C, 38.85; H, 8.76; N, 2.48.

Example 10

N-Ethyl-N,N-dipropyl-N-isobutyl ammonium bromide terminated polydimethyl siloxanes (7b)

FTIR: 3395, 2964, 2790, 2513, 1589, 1454, 1416, 1254, 1104, 1019 $cm^{-1}$, $^1H$ NMR (CDCl3): 2.98-2.78 (m, 12H), 2.60-2.52 (m, 4H), 2.15-2.11 (in, 2H), 1.51 (t, 6H), 1.43-1.34 (m, 8H), 1.27 (d, 6H), 1.13 (t, 12H), 0.66-0.61 (m, 4H), 0.12-0.01δ (m, 66H). A pale yellow waxy solid was afforded in 62% yield. Anal. Caled. range: C, 41.64-40.14; H, 9.08-8.93; N, 2.43-2.04. Found: C, 40.76; H, 9.02; N, 2.35.

Example 11

N-Ethyl-N,N-dibutyl-N-isobutyl ammonium bromide terminated polydimethyl siloxanes (7c)

FTIR: 3433, 2960, 2779, 2679, 2521, 1943, 1593, 1462, 1412, 1263, 1119, 1008 $cm^{-1}$, $^1$NMR (CDCl3): 3.21-3.02 (m, 12H), 2.89-2.74 (m, 4H), 2.30 (m, 2H), 1.53 (t, 6H), 1.21 (d, 6H), 1.02-0.93 (m, 12H), 0.62-0.57 (4H), 0.11-0.01δ (m, 66H). A pale yellow waxy solid was afforded in 71% yield, Anal. Caled. range: C, 43.68-41.92; H, 9.33-9.15; N, 2.32-1.96. Found: C, 42.23; H, 9.22; N, 2.09.

Example 12

N-Ethyl-N,N-dipentyl-N-isobutyl ammonium bromide terminated polydimethyl siloxanes (7d)

FTIR: 3391, 2964, 2871, 2787, 1466, 1412, 1262, 1092, 1023 $cm^{-1}$, $^1H$ NMR (CDCl3): 3.25-3.14 (m, 12H), 2.92-2.69 (in, 4H), 2.11-2.08 (m, 2H), 1.51 (t, 6H), 1.37-1.26 (m, 24H), 1.28 (d, 6H), 0.98 (t, 12H), 0.66-0.62 (m, 4H), 0.21-0.05δ (m, 66H). A pale yellow solid was afforded in 68% yield. Anal. Calcd. range: C, 45.54-43.57; H, 9.55-9.34; N, 2.21-1.88. Found: C, 44.48; H, 9.19; N, 2.49.

Example 13

N-Ethyl-N,N-dibexyl-N-isobutyl ammonium bromide terminated polydimethyl siloxanes (7e)

FTIR: 3407, 2956, 2794, 2683, 2525, 1578, 1462, 1408, 1254, 1096, 1015 $cm^{-1}$. $^1H$ NMR (CDCl3): 3.29-3.24 (m, 12H), 2.99-2.91 (m, 4H), 2.19-2.11 (m, 2H), 1.56 (t, 6H), 1.38-1.24 (m, 38H), 0.94 (t, 12H), 0.66-0.61 (m, 4H), 0.12-0.11δ (m, 66H). A pale yellow solid was afforded in 58% yield. Anal. Calcd. range: C, 47.10-45.10; H, 9.76-9.53; N, 2.12-1.81. Found: C, 46.92; H, 9.41; N, 2.01.

Example 14

N-Ethyl-N,N-dioctadexyl-N-isobutyl ammonium bromide terminated polydimethyl siloxanes (7f)

FTIR: 3407, 2948, 2848, 2798, 2740, 2675, 2513, 1963, 1578, 1474, 1404, 1370, 1258, 1100, 1015 $cm^{-1}$. $^1H$ NMR (CDCl3): 3.25-3.17 (m, 12H), 2.94-2.87 (m, 4H), 1.99-1.94 (m, 2H), 1.53 (t, 6H), 1.32-1.21 (m, 126H), 0.89 (t, 12H), 0.66-0.62 (m, 4H), 0.17-0.01δ (m, 66H). A pale yellow solid was afforded in 50% yield, Anal. Calcd. range: C, 60.19-57.40; H, 11.31-11.00; N, 1.40-1.26. Found: C, 57.94; H, 11.30; N, 1.39.

Example 15

Bacterial Challenge Preparation and Antimicrobial Testing Protocol

General Procedure for Preparation of Growth Media—

To a 1-L Erlenmeyer flask equipped with a stir bar was added 25.7 g Letheen broth™ (Difco Laboratories, Detroit, Mich.) and 1 L Milli-Q® filtered water. The mixture was stirred over low heat for 30 min. Aliquots (4.5 mL) of the resulting solution were added to autoclavable culture tubes (~200) to be used in subsequent serial dilutions. The test tubes were covered with plastic lids and autoclaved at 121° C. (and 15 psi) for 25 min. Letheen broth was selected for its ability to neutralize the biocidal effect of quaternary ammonium salts so that continued antibacterial action would not occur after the serial dilution step.

Preparation of Bacteria—

*Staphylococcus aureus* cells were grown in our laboratory according to standard microbiological techniques. *S. aureus* was harvested from an agar plate by removing a single CFU (colony forming unit), with a sterile inoculating loop, and placing it in Letheen broth. The culture was incubated at 28-30° C. overnight in a shaking incubator. The cells were then pelleted by centrifugation at 3000 rpm and 18° C. The cells were then resuspended in 0.5% saline solution to achieve a density of about $10^7$ CFU/ML as determined by McFarland turbidity standards.

Procedure for Challenge Tests—

This method of evaluation is a well established serial dilution screening that has been employed by many research groups for decades (Madigan et al., Brock Biology of Microorganism, 11th ed. Prentice Hall: Carbondale, Ill., (2005); MaeLowry et al., *Appl. Microbiol.,* 20, 46 (1970)). A 1-mL aliquot of each water soluble ionic biocide was added to 1 mL of $10^7$ CFU previously resuspended *S. aureus*. The resulting solution was vortexed and allowed to incubate at room temperature for 2 h. Afterwards, the resulting solution was serially diluted in Letheen broth and allowed to incubate at 35° C. for 24 h. The tubes were read at the end of the 24-h incubation period. Positive growth was indicated by the presence of string-like filamentous growth of colonies of bacteria in solution, not mere murkiness, which may result form other forms of contamination. All data reported are an average of triplicates, and data is reported as log-reduction from a starting concentration of $10^7$ CFU/mL.

Example 15

Monitoring Technique for Movement of Liquids

Movement of all liquids in this study was monitored optically with the use of an Intel-QX5 microscope at a magnification power of 10×. In all cases, photos were captured and stored electronically every 2 s for 5 min and, subsequently, every 5 min for 24 h. In most cases, 20 data points were taken from the first 5 min of data collection. Plotting additional data points resulted in a graph that was difficult to interpret because of overlapping data points that provided no additional useful information. It was noticed in most cases that the rate of change remained constant after the first 5 min, and therefore the remainder of the data points were not plotted to facilitate viewing the most useful data.

All liquid movement measurements were made on precleaned glass microscope slides in the horizontal position. A 1-mL aliquot of each liquid was placed on the center of the microscope slide using a calibrated micropipette. Because of the transparency of the microscope slide and the wide field of focus of the microscope at 10× power, a scale was placed under the glass slide. This resulted in the scale being recorded along with the movement of the various liquids. It was discovered that ambient dust frequently entered the spreading liquid and resulted in the liquid spreading in a noncircular pattern. Therefore, the use of a microscope slide as a protective cover along with spacers was necessary to prevent contamination from airborne dust particles present in the laboratory. The spacers prevented a sandwiching effect, while at the same time allowing air currents to affect the sample as they typically would in an open ambient environment. The use of an additional external light source was necessary to create a faint shadow to better visualize the advancing edge of the thinning liquid. It was discovered that the leading edge of the spreading liquid was best visualized with the naked eye; however, the need to make periodic measurements and accurately record the movement required the use of the low power microscope. All data was collected under ambient conditions to best simulate real world conditions.

After the liquids were allowed to spread, the video was examined and measurements were made for the average diameter of the advancing edges. The movement of all liquids reported is the average of three trials. All data was normalized to the initial liquid drop size at $T_0$. In those examples where the spread was not perfectly circular, multiple measurements of diameters were made and the average of those Obtained was used for plotting. The average change in diameter was plotted because of the errors encountered when attempting to use electronic software to calculate the area of the spreading liquid from the video. This was attributed to shadowing effects in the captured video.

All microscope slides and silicon wafers were cleaned prior to use for spreading studies. The manufacturer's pretreatment was removed by first soaking in chloroform and allowing the substrates to dry. The substrates were then soaked in an alcoholic potassium hydroxide solution for 2 h. After base treatment, the slides were washed with copious amounts of deionized water. Slides were dried in an oven and immediately used. Care was taken not to store cleaned substrates for prolonged periods of time to prevent contamination by ambient organics or dust particles.

Example 16

Comparison of Spreading of PDMS to Other Liquids

A variety of oils and lubricants were evaluated for their ability to wet a freshly cleaned glass substrate. As shown in FIG. 1, the methyl-terminated PDMS possessed the highest rate of spread for those liquids evaluated. Soybean cooking oil, scientific vacuum pump oil, and commercial 15W40 motor oil all had very similar rates of spread. The rate of spread of these liquids was also compared to that of water on the same surface. As expected, water had the lowest rate of spread due to hydrogen bonding and high surface energy. From these results, it was believed that the addition of a surfactant to deionized water should affect its spreadability on the glass substrate. An aliquot of deionized water containing 0.001% (w/w) tetrabutylammonium bromide surfactant was examined. It was discovered that the rate of spread of the surfactant containing water wetted the surface more, initially; however, did not spread. Similarly, a solution containing 0.01% (w/w) surfactant was also examined with similar results. In both cases, the water containing surfactant spread more than water, alone; however, neither spread as well as the other commercial oils examined. The plots of water with surfactant were omitted from FIG. 1 for improved viewing.

As a result of examining a variety of commercial products, the self-spreading properties of the silicone oil (PDMS) far exceeded any other material examined. Consequently, it was concluded that the spread of the liquid was due to a combination of effects such as polarity, viscosity, surface energy, and the ability to conform to a variety of surfaces because of a flexible backbone, thus facilitating movement of the liquid across the substrate. As expected, molecules with a high degree of hydrogen bonding did not exhibit a high rate of spread.

Example 17

Comparison of Spreading of PDMS of Varying Molecular Weight

Figure 2:
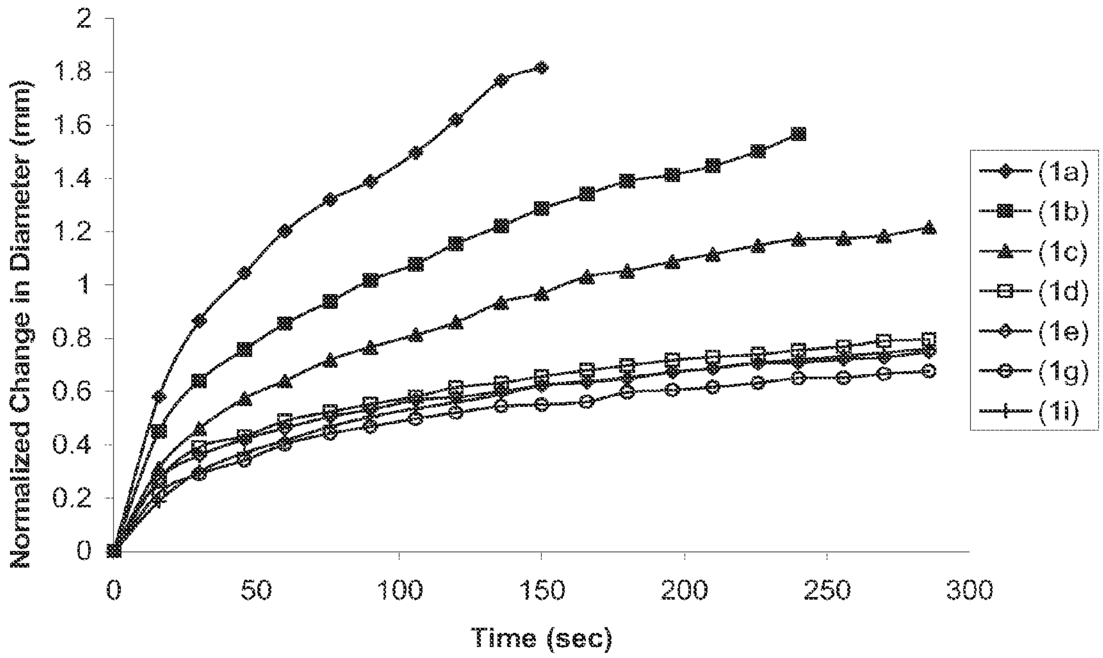
FIG. 2 shows a comparison of the rate of movement of methyl-terminated PDMS by molecular weight/viscosity.

A variety of commercially available methyl-terminated PDMS was examined in a similar study to determine which molecular weight PDMS provided optimum mobility (Table 1). An inverse correlation between the molecular weight of the PDMS oligomers and the rate of spread was observed (FIG. 2). It was concluded that the relative viscosities of the molecules examined played a major role in dictating the self-spreading properties. The low surface energy molecules deformed and moved as anticipated for all examples investigated (1a-i). Because of the similarity in movement of compounds 1d-i, one compound (1f) is omitted from FIG. 2 for optimal viewing clarity,

TABLE 1

| # | $M_W$ | Viscosity (cSt) (±10%) |
|---|---|---|
| 1a | 550 | 3.0 |
| 1b | 950 | 7.0 |
| 1c | 1250 | 10 |
| 1d | 2000 | 20 |
| 1e | 5970 | 100 |
| 1f | 13,650 | 350 |
| 1g | 28,000 | 1000 |
| 1h | 49,350 | 5000 |
| 1i | 116,500 | 60,000 |

Example 18

Comparison of N,N,N-trialkyl-N-propyl ammonium bromide terminated polydimethylsiloxanes In an attempt to increase antimicrobial activity while at the same time attempting to maintain the self-spreading properties of PDMS, only two ionic functionalities were incorporated within the molecule, one at each terminus. It was believed that this would lower the overall hydrogen bonding interactions of the molecule to the surface and in turn promote self-spreading of the molecule while also promoting antimicrobial activity. The homologous series of molecules were synthesized in good yield and because of their unique physical properties, they were easily purified. It was found that by using an excess of alkyl halide, the reaction was forced to completion while facilitating removal of excess alkyl halide and solvent under reduced pressure. This procedure afforded a product of sufficient purity for use in this study. If desired, a purer product can be obtained via trituration with ethyl ether.

Using the biological protocol described earlier, each hybrid PDMS compound (5a-f) was evaluated in a solution test and the results are shown in Table II. A trend very similar to other traditional quaternary ammonium biocides was discovered. For the molecules examined, antimicrobial activity increased with the increased length of alkyl chain. Compounds 5d-f clearly exhibited greater antimicrobial properties against the subjected Gram-positive bacteria. It was concluded that the direct attachment of the quaternary ammonium functionality to the PDMS backbone did not minimize the biological effect because of polarity or surface energy. Furthermore, it was concluded that the presence of three long alkyl groups directly attached to the quaternary nitrogen did not hinder antimicrobial activity because of steric effects, as has been observed in more widely used dimethyl ammonium series (frequently found in common household biocidal products). These results served as supporting evidence for a theory that possible coiling of the target molecules may result in reduced antimicrobial activity.

TABLE 2

| # | R | $M_W$ | *S. aureusa*[a] |
|---|---|---|---|
| 5a | —$C_2H_5$ | 900-1000 | 2 |
| 5b | —$nC_3H_7$ | 900-1000 | 2.6 |
| 5c | —$nC_4H_9$ | 900-1000 | 2.3 |
| 5d | —$nC_5H_{11}$ | 900-1000 | 4 |
| 5e | —$nC_6H_{13}$ | 900-1000 | 6 |
| 5f | —$nC_{18}H_{37}$ | 900-1000 | 7 |

[a]Log reduction results from solution testing; difference observed when 1 mL of $10^7$ CFU/mL *S. aureus* was placed in 1 mL of water soluble ionic biocide.

Figure 3:
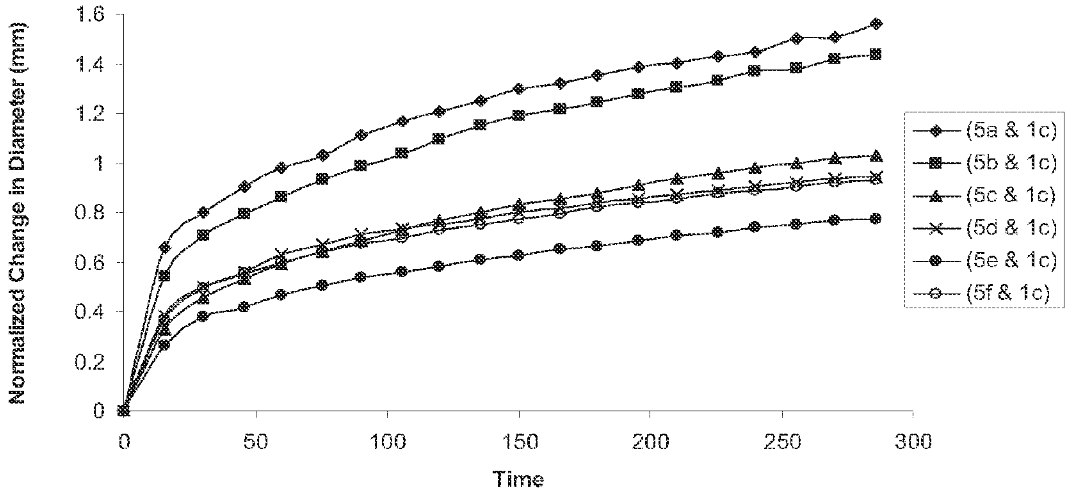
FIG. 3 shows a comparison of the rate of spread of homologous series (5) blended with PDMS (1c).

Movement was improved by blending with compound 1c, Compound 5 was blended with 1c in a 60:40 ratio (w/w) and then subjected to spread studies that are graphically depicted in FIG. 3. Although compounds 5e and 5f afforded the greatest antimicrobial activity, they were the least mobile. Compounds 5a and 5b resulted in the greatest rate of spread with the least biological activity; thus, supporting the idea that an inverse correlation exists between chain length and antimicrobial properties.

Example 18

Comparison of N,N,N-trialkyl-N-isobutyl ammonium bromide terminated polydimethylsiloxanes Each oligomer from Examples 9-14 was subjected to solution antimicrobial evaluation and afforded good results. As seen in the data for compounds 5a-f, there was a direct correlation with antimicrobial properties and alkyl chain length. Although very similar, the antimicrobial properties of compound 5f appear to be marginally greater than those exhibited by any of the compounds 7a-f (Table 3).

TABLE 3

| # | R | $M_W$ | *S. aureusa*[a] |
|---|---|---|---|
| 7a | —$C_2H_5$ | 800-1000 | 2 |
| 7b | —$nC_3H_7$ | 800-1000 | 3 |
| 7c | —$nC_4H_9$ | 800-1000 | 3.6 |
| 7d | —$nC_5H_{11}$ | 800-1000 | 4.3 |
| 7e | —$nC_6H_{13}$ | 800-1000 | 6 |
| 7f | —$nC_{18}H_{37}$ | 800-1000 | 6 |

[a]Log reduction results from solution testing; difference observed when 1 mL of $10^7$ CFU/mL *S. aureus* was placed in 1 mL of water soluble ionic biocide.

Figure 4:
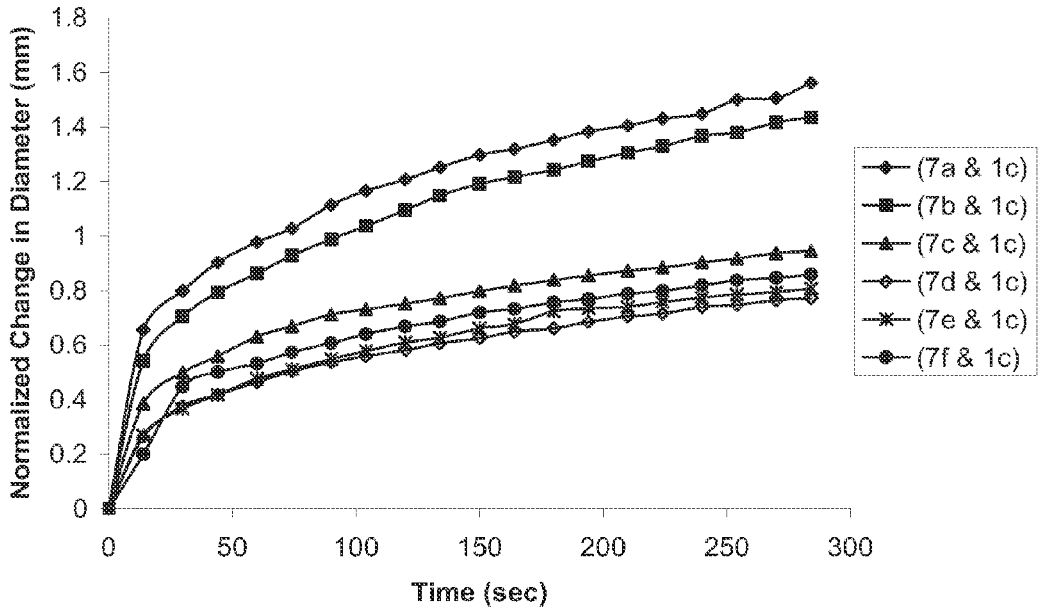
FIG. 4 shows the rate of spread of homologous series (7) blended with PDMS (1c) (60:40 ratio).

After observing similar to slightly reduced antimicrobial properties for 7 (when compared to 5), a similar study of spread was performed. The physical properties of 7 were very similar to those described earlier for compounds 5a-f. Therefore, spread measurements were performed as a blend with 1c in a 60:40 ratio (w/w) as described previously and are depicted in FIG. 4. Very similar results were seen for this homologous series as well. Although compounds 7e and 7f afforded the greatest antimicrobial activity, they resulted in very little spread. Compounds 7a and 7b resulted in the greatest rate of spread with least antimicrobial activity. These results are in agreement with the test data for compounds 5a-f.

Example 19

Spreading on Silicon

Figure 5:
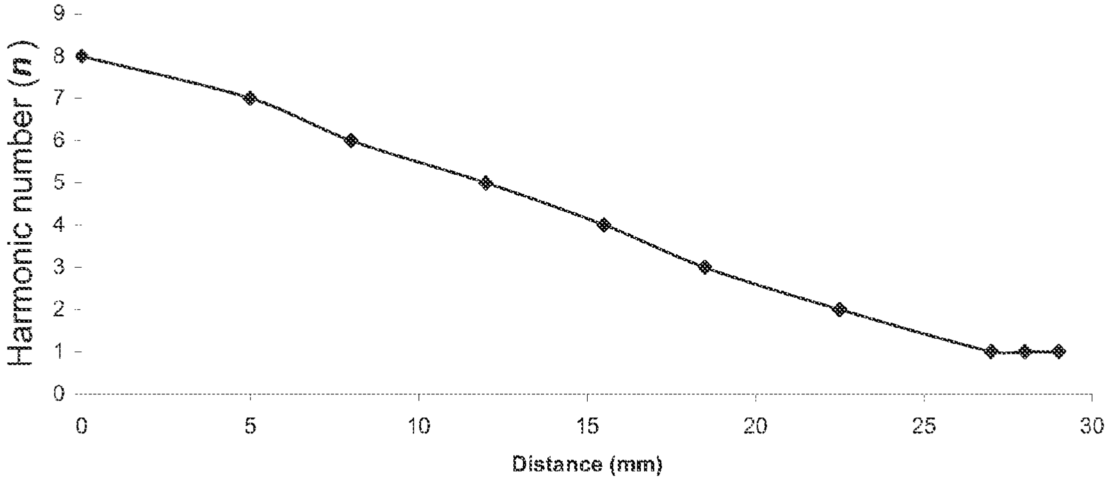
FIG. 5 illustrates the relative spreading profile of the liquid.

As the previous examples were conducted on glass, the ability of a blend of compound 5b and 1c (60:40) (w/w) to self-spread on a previously cleaned silicon wafer was examined. A 1-mL sample of the blend was placed in the center of a 2-in diameter silicon wafer. Interference patterns began to form after a few hours and continued to develop with time. Interference patterns developed after allowing the mixture to spread for 24 h. The presence of interference fringe patterns in thin liquid films indicates film thickness is on the same order of magnitude as the wavelength of light. Maximum intensities in the pattern are observed when the film thickness is a multiple of [¼] of the wavelength of the reflected light. With additional time, the liquid continued to spread on the wafer and the observed rainbow interference pattern became a uniform violet color indicating that the thickness of the liquid on the wafer was uniformly approaching [¼] the wavelength of light. After allowing the coated wafer to sit for an extended period of time, the liquid eventually spread off of the edge of the wafer and coated the bottom of the wafer and began to coat the Petri dish in which the wafer had been placed to protect it from ambient dust. Since the film thickness varied from thicker to thinner in a uniform manner, as the film spread a series of "rainbows" appear; a new one every time the film thickness decreased by a multiple of [¼] of the wavelength of the given "color." FIG. 5 illustrates the relative spreading profile of the liquid. The graph correlates harmonic number (n), also referred to frequently as multiples of wavelength of any specified color band, to distance across the wafer. Preliminary approximations were made given the amount of liquid applied and the surface area of the wafer. If the liquid were allowed to spread to form a uniform coating, it is anticipated that the thickness of the liquid should approach 500 nm. As can be seen from the profile of the advancing edge using this methodology, it is very consistent with that of previous reports (Bascom, *Wear,* 39, 185 (1976)).

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. A polymer comprising the formula:

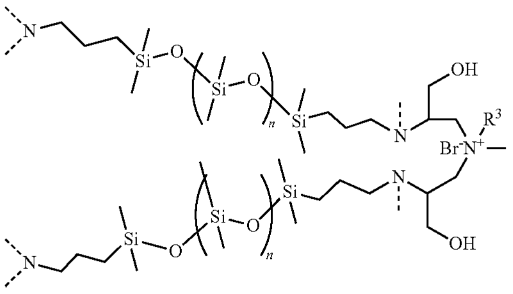

-continued

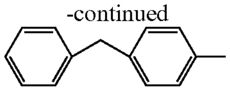

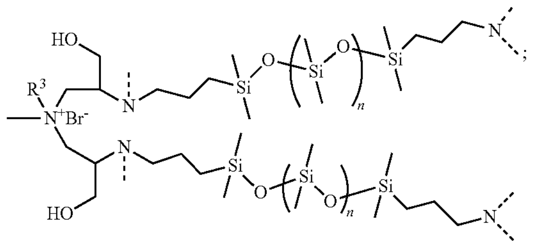

wherein $R^3$ is an independently selected alkyl group;

wherein n is a positive integer; and wherein each dashed bond indicates binding to a dipropyl polydimethylsilaxane group.

2. A polymer comprising the formula:

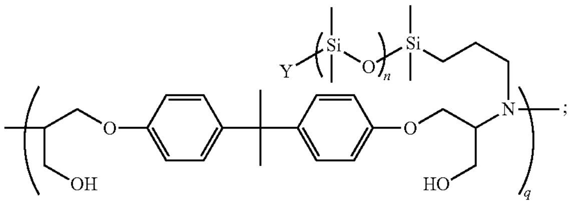

wherein n and q are independently selected positive integers; and wherein Y is methyl or

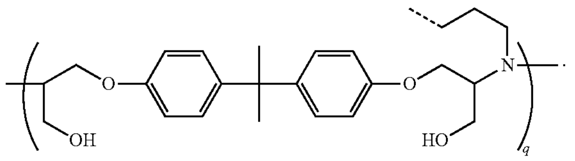

* * * * *